US011325090B1

(12) United States Patent
Weissman et al.

(10) Patent No.: US 11,325,090 B1
(45) Date of Patent: May 10, 2022

(54) CATALYTIC SOLAR REACTOR (71) Applicant: Precision Combustion, Inc., North Haven, CT (US)

(72) Inventors: Jeffrey G Weissman, Guilford, CT (US); Bruce Crowder, Hamden, CT (US); Julian Prada, Philadelphia, PA (US)

(73) Assignee: Precision Combustion, Inc., North Haven, CT (US)

( * ) Notice: Subject to any disclaimer, the term of this patent is extended or adjusted under 35 U.S.C. 154(b) by 0 days.

(21) Appl. No.: 17/097,048

(22) Filed: Nov. 13, 2020

Related U.S. Application Data (60) Provisional application No. 62/945,309, filed on Dec. 9, 2019.

(51) Int. Cl.
*B01J 12/00* (2006.01)
*B01J 19/24* (2006.01)
(Continued)

(52) U.S. Cl.
CPC ......... *B01J 12/007* (2013.01); *B01J 19/0013* (2013.01); *B01J 19/127* (2013.01);
(Continued)

(58) Field of Classification Search
CPC .. B01J 12/007; B01J 19/0013; B01J 19/2495; B01J 2219/00076; B01J 2219/00157;
(Continued)

(56) References Cited

U.S. PATENT DOCUMENTS 4,083,695 A    4/1978 Haese
4,395,623 A *  7/1983 Shimada ............... H05B 3/141
                                                   219/505

(Continued)

FOREIGN PATENT DOCUMENTS

EP         3212323 B1   10/2018
WO    WO 2010/014217 A1    2/2010
(Continued)

OTHER PUBLICATIONS

C. Agrafiotis, H. V. Storch, M. Roeb, C. Sattler, "Solar Thermal Reforming of Methane Feedstocks for Hydrogen and Syngas Production—A Review," Renewable and Sustainable Energy Reviews 29 (2014) 656-682.

(Continued)

*Primary Examiner* — Matthew J Merkling
(74) *Attorney, Agent, or Firm* — Marie Zuckerman; Andrew D. Gathy (57) ABSTRACT

A catalytic solar reactor useful in chemical processes, more particularly, useful in endothermic chemical processes. The reactor comprises a reaction pathway defined by an exterior wall and an interior wall, the exterior wall comprising a solar radiation receiver capable of converting solar radiation into heat and transmitting the heat to the reaction pathway. Further, the reaction pathway has disposed therein, in alternating fashion, a plurality of catalytic elements and a plurality of heat transfer elements. Optionally, a supplementary heater, such as a conventional fossil fuel burner, is disposed in a plenum located within the interior of the reactor. The heater is employed as a supplemental source of heat, for example, when solar radiation is unavailable.

23 Claims, 7 Drawing Sheets

(51) Int. Cl.
*C01B 3/38* (2006.01)
*C01B 3/48* (2006.01)
*C07C 1/04* (2006.01)
*B01J 19/00* (2006.01)
*B01J 19/12* (2006.01)

(52) U.S. Cl.
CPC ........... *B01J 19/2495* (2013.01); *C01B 3/384* (2013.01); *C01B 3/48* (2013.01); *C07C 1/041* (2013.01); *B01J 2219/00076* (2013.01); *B01J 2219/00157* (2013.01); *C01B 2203/0233* (2013.01); *C01B 2203/0238* (2013.01); *C01B 2203/0283* (2013.01); *C01B 2203/062* (2013.01); *C01B 2203/0811* (2013.01); *C01B 2203/0833* (2013.01); *C01B 2203/1241* (2013.01)

(58) Field of Classification Search
CPC ... C01B 3/384; C01B 3/48; C01B 2203/0238; C01B 2203/0233; C01B 2203/062; C01B 2203/0811; C01B 2203/0833; C01B 2203/1241
See application file for complete search history.

(56) References Cited

U.S. PATENT DOCUMENTS

| | | | |
|---|---|---|---|
| 4,552,741 A * | 11/1985 | Melchior | C01B 3/26 423/359 |
| 5,051,241 A | 9/1991 | Pfefferle | |
| 5,229,079 A * | 7/1993 | Harada | H05B 3/12 422/174 |
| 5,465,573 A * | 11/1995 | Abe | F01N 13/0097 60/274 |
| 6,156,444 A | 12/2000 | Smith | |
| 6,328,936 B1 | 12/2001 | Roychoudhury | |
| 6,955,792 B2 | 10/2005 | Filippi | |
| 7,141,092 B1 | 11/2006 | Roychoudhury | |
| 7,325,401 B1 | 2/2008 | Kesseli | |
| 8,603,407 B2 | 12/2013 | Pfefferle | |
| 9,446,365 B2 | 9/2016 | Junaedi | |
| 10,076,739 B1 | 9/2018 | Weissman | |
| 2003/0182861 A1* | 10/2003 | Weimer | C01B 3/344 48/197 R |
| 2005/0262817 A1* | 12/2005 | Hatanaka | F01N 3/0217 55/282.3 |
| 2008/0173533 A1* | 7/2008 | Mankins | C01B 3/32 204/157.15 |
| 2010/0022785 A1 | 1/2010 | Hechler | |
| 2010/0276336 A1 | 11/2010 | Ferschneider | |
| 2013/0004801 A1* | 1/2013 | Henry | H01M 8/0606 429/9 |
| 2013/0025192 A1* | 1/2013 | Wegeng | F22B 1/006 44/457 |
| 2013/0334465 A1* | 12/2013 | Zhao | B01J 7/02 252/373 |
| 2015/0054284 A1 | 2/2015 | Nathan | |
| 2016/0023898 A1* | 1/2016 | Morgenstern | B01J 8/0221 48/61 |
| 2016/0052853 A1 | 2/2016 | Dubois | |
| 2019/0346177 A1* | 11/2019 | Jafarian | C01B 3/042 |

FOREIGN PATENT DOCUMENTS

| | | |
|---|---|---|
| WO | WO 2017/102096 A1 | 6/2017 |
| WO | WO 2018/127562 A1 | 7/2018 |

OTHER PUBLICATIONS

N.E.Tsakoumis, M. Ronning, O. Borg, E. Ryttera, A. Holmen, "Deactivation of Cobalt Based Fischer-Tropsch Catalysts: A Review," Catalysis Today 154 (2010) 162-182.

C. Perego, R. Bortolo, R. Zennaro, "Gas to Liquids Technologies for Natural Gas Reserves Valorization: The Eni Experience," Catalysis Today, 142 (2009) 9-16.

C. Visconti, E. Tronconi, L. Lietti, G. Groppi, P. Forzatti, C. Cristiani, R. Zennaro, S. Rossinni, "An Experimental Investigation of Fischer-Tropsch Synthesis Over Washcoated Metallic Structured Supports," Applied Catalysis A: General, 370 (2009) 93-101.

J.F. Munera S. Irusta, L.M. Cornaglia, E.A Lombardo, D.V. Cesar, M. Schmal, "Kinetics and Reaction Pathway of the CO2 Reforming of Methane on Rh Supported on Lanthanum-Based Solid." Journal of Catalysis 245 (2007) 25-34.

Co-Pending unpublished non-provisional patent application, U.S. Appl. No. 17/097,016, filed Nov. 13, 2020, entitled "Catalytic Reactor," Applicant Precision Combustion, Inc.

Co-Pending unpublished non-provisional patent application, U.S. Appl. No. 16/273,234, filed Feb. 12, 2019, entitled "Process for Converting Alkanes to Olefins," Applicant Precision Combustion, Inc.

Co-Pending unpublished non-provisional patent application, U.S. Appl. No. 17/015,796, filed Sep. 9, 2020, entitled "Regenerable Adsorbent System," Applicant Precision Combustion, Inc.

* cited by examiner

CATALYTIC SOLAR REACTOR

CROSS-REFERENCE TO RELATED APPLICATIONS

This application claims benefit of U.S. provisional patent application No. 62/945,309, filed Dec. 9, 2019.

GOVERNMENT RIGHTS

This invention was made with support from the United States government under Contract no. DE-SC0015855, awarded by the Department of Energy. The United States government has certain rights in the invention.

FIELD OF THE INVENTION

This invention pertains to a catalytic solar reactor useful primarily in endothermic chemical processes and also useful, under certain circumstances, in exothermic chemical processes. This invention also pertains to a generic method of conducting a chemical process; and more specifically, to a method of conducting an endothermic chemical process; and even more specifically, to a method of conducting a dry reforming process of converting a mixture of methane and carbon dioxide into a synthesis gas mixture comprising hydrogen and carbon monoxide.

BACKGROUND OF THE INVENTION

Catalytic solar reactors are known in the art as described, for example, in PCT patent application publication WO 2018/127562 (12 Jul. 2018). Such reactors are known for facilitating endothermic chemical processes, wherein heat required for the process is obtained from solar radiation rather than from burning fossil fuels. Generally, such reactors are constructed from a solar radiation receiver having disposed therein a reaction pathway containing a supported catalyst. The prior art discloses that the catalyst can be deposited upon a support or "substrate", such as structured pellets, foam, or a ceramic monolith. Disadvantageously, the disclosed supports are not readily adapted to the shape of the solar radiation receiver, which is often designed with geometric points and sharp angles so as to maximize collection of solar radiation and minimize radiation scattering to the environment. Moreover, the prior art does not disclose a simple interface of such reactors with a traditional fossil fuel burner that would be able to generate heat when solar radiation is unavailable. Also, prior art catalytic solar reactors are not adapted to modulate and control heat transfer into and out of the reactor, and thereby modulate and control the catalytic reaction occurring therein.

In view of the above, the design of catalytic solar reactors would benefit from several improvements. In particular, it would be desirable to provide the catalyst on a flexible and readily available substrate support amenable to any solar reactor design and shape, regardless of sharp points and angular dimensions. It would be more desirable to provide a catalytic solar reactor that incorporates, in a simple design, a fossil fuel burner so that the reactor is operative not only on sun-filled days but during off-times when solar radiation is unavailable, particularly, at nighttime and during inclement weather. Further, it would be desirable to provide a catalytic solar reactor that has the capability to modulate and control catalytic reaction rates of chemical processes occurring therein by controlling heat transfer into and out of the reaction pathway.

SUMMARY OF THE INVENTION

In one aspect, this invention provides for a catalytic solar reactor comprising: a reaction pathway having a reactor inlet and a reactor outlet, the reaction pathway bounded by an exterior wall and an interior wall; wherein the exterior wall comprises a solar radiation receiver disposed in thermal communication with the reaction pathway; and further wherein the reaction pathway has disposed therein the following structures:

(a) a plurality of catalytic elements, each catalytic element comprising a porous material having a catalyst supported thereon, each catalytic element further comprising a first flowpath from a first inlet side to a first outlet side;

(b) a plurality of heat transfer elements, each heat transfer element comprising a porous, thermally-conductive material substantially lacking catalytic activity; each heat transfer element further comprising a second flowpath from a second inlet side to a second outlet side; and (c) further wherein the plurality of catalytic elements and the plurality of heat transfer elements are disposed within the reaction pathway in an alternating configuration defining a fluid flowpath from each element inlet side to each element outlet side.

The catalytic solar reactor of this invention is suitably employed in any generic endothermic chemical process requiring an input of heat. In one embodiment, the catalytic solar reactor of this invention is suitably employed in an endothermic reaction of reforming a mixture of methane and carbon dioxide to produce a synthesis gas mixture comprising hydrogen and carbon monoxide, as seen in Eqn. (1):

$$CO_2 + CH_4 \rightarrow 2H_2 + 2CO \qquad \text{(Eqn. 1)}$$

Under operating conditions in the apparatus of this invention, wherein the heat transfer elements are interspersed between the catalytic elements, carbon formation is significantly reduced while methane conversion is significantly increased.

Additional endothermic processes capable of being conducted in the apparatus of this invention include, but are not limited to, the following embodiments illustrated in Equations 2-5. Combinations of these processes can also be employed.

Reverse water gas shift in which carbon dioxide reacts with hydrogen to form a mixture of carbon monoxide and water:

$$CO_2 + H_2 \rightarrow CO + H_2O \qquad \text{(Eqn. 2)}$$

Methane steam reforming in which methane reacts with water to form a mixture of carbon monoxide and hydrogen:

$$CH_4 + H_2O \rightarrow CO + 3H_2 \qquad \text{(Eqn. 3)}$$

Steam reforming of hydrocarbons in which a hydrocarbon or mixture thereof reacts with water to form a mixture of carbon monoxide and hydrogen:

$$C_nH_m + nH_2O \rightarrow nCO + (n+m/2)H_2 \qquad \text{(Eqn. 4)}$$

Carbon dioxide reforming of hydrocarbons in which a hydrocarbon or mixture thereof reacts with carbon dioxide to form a mixture of carbon monoxide and hydrogen:

$$C_nH_m + nCO_2 \rightarrow 2nCO + (m/2)H_2 \qquad \text{(Eqn. 5)}$$

The catalytic solar reactor of this invention is also useful in exothermic chemical processes particularly where heat generated by the chemical process itself is insufficient to obtain optimal reaction rate or performance; and therefore, the reaction is improved by an input of heat. In one embodiment, for example, the catalytic solar reactor of this invention is successfully employed in an exothermic Fisher-Tropsch process of converting synthesis gas, namely a mixture of carbon monoxide and hydrogen, into one or more C6+ liquid hydrocarbons, as exemplified by Eqn. (6):

$$6CO + 13H_2 \rightarrow C_6H_{14} + 6H_2O \tag{Eqn. 6}$$

Accordingly, in another aspect, this invention provides for a method of conducting a chemical process, comprising:

(a) providing a catalytic solar reactor comprising a reaction pathway having a reactor inlet and a reactor outlet, the reaction pathway bounded by an exterior wall and an interior wall; wherein the exterior wall comprises a solar radiation receiver disposed in thermal communication with the reaction pathway; and further wherein the reaction pathway has disposed therein the following structures:
- (a)(i) a plurality of catalytic elements, each catalytic element comprising a porous material having a catalyst supported thereon, each catalytic element further comprising a first flowpath from a first inlet side to a first outlet side;
- (a)(ii) a plurality of heat transfer elements, each heat transfer element comprising a porous, thermally-conductive material substantially lacking catalytic activity; each heat transfer element further comprising a second flowpath from a second inlet side to a second outlet side; and
- (a)(iii) further wherein the plurality of catalytic elements and the plurality of heat transfer elements are disposed within the reaction pathway in an alternating configuration defining a fluid flowpath from each element inlet side to each element outlet side;

(b) exposing the solar radiation receiver to solar radiation so as to transfer heat to the reaction pathway;

(c) feeding a reactant stream through the thusly-heated reaction pathway from each element inlet side to each element outlet side; and (d) contacting the reactant stream with the catalyst as the reactant stream passes through the reaction pathway, the contacting occurring under process conditions sufficient to produce a product stream.

The catalytic solar reactor and the method of this invention provide several advantages as compared with the prior art. As explained in detail hereinafter, in a preferred embodiment, the porous material supporting the catalyst is constructed of a flexible, ultra-short-channel-length material that is readily adapted to the shape of any reaction pathway, as dictated by the shape and angular configuration of the solar radiation receiver. Additionally, the catalytic solar reactor of this invention comprises a unique internal structure of alternating catalytic elements and heat transfer elements that advantageously allows for modulating and controlling heat transfer into and out of the reactor, and as a consequence modulating and controlling catalytic reaction rates and performance of the reaction occurring within the reaction pathway.

As an added benefit, the catalytic solar reactor of this invention is easily integrated with a supplementary heat generator, such as a conventional fossil fuel burner or any other conventional reactor capable of supporting an exothermic process, so as to generate supplementary heat, for example, at nighttime and during inclement weather or whenever else solar radiation collection is unavailable. Aside from combustion or burning of fossil fuel, the supplementary heat generator can be employed to provide additional heat to the catalytic solar reactor through other exothermic processes including, but not limited to, the embodiments illustrated by Equations 7-12:

Partial oxidation of hydrocarbons, wherein a hydrocarbon is partially oxidized in the presence of oxygen to produce synthesis gas:

$$C_nH_m + 0.5nO_2 \rightarrow nCO + (m/2)H_2 \tag{Eqn. 7}$$

Sabatier reaction, wherein a mixture of carbon dioxide and hydrogen is converted into a mixture of methane and water:

$$CO_2 + 4H_2 \rightarrow CH_4 + 2H_2O \tag{Eqn. 8}$$

Forward water gas shift, wherein a mixture of carbon monoxide and water is converted into a mixture of carbon dioxide and hydrogen:

$$CO + H_2O \rightarrow CO_2 + H_2 \tag{Eqn. 9}$$

Carbon monoxide oxidation, wherein carbon monoxide is oxidized with oxygen to form carbon dioxide:

$$CO + 0.5O_2 \rightarrow CO_2 \tag{Eqn. 10}$$

Fischer-Tropsch reaction, wherein carbon monoxide is reacted with hydrogen to form one or more hydrocarbons and water:

$$nCO + (n+m)H_2 \rightarrow C_nH_{2m} + nH_2O \tag{Eqn. 11}$$

Bosch reaction, wherein carbon dioxide is reacted with hydrogen to form carbon and water:

$$CO_2 + 2H_2 \rightarrow C + 2H_2O \tag{Eqn. 12}$$

DETAILED DESCRIPTION OF THE INVENTION

In one embodiment, this invention provides for a catalytic solar reactor comprising: a reaction pathway having a reactor inlet and a reactor outlet, the reaction pathway bounded by an exterior wall and an interior wall; wherein the exterior wall comprises a solar radiation receiver disposed in thermal communication with the reaction pathway; and further wherein the reaction pathway has disposed therein the following structures:

(a) a plurality of catalytic elements, each catalytic element comprising a porous material having a catalyst supported thereon; the porous material comprising a mesh having an ultra-short-channel-length; and further wherein each catalytic element further comprises a first flowpath from a first inlet side to a first outlet side;

(b) a plurality of heat transfer elements, each heat transfer element comprising a porous, thermally-conductive material substantially lacking catalytic activity; each heat transfer element further comprising a second flowpath from a second inlet side to a second outlet side; and (c) further wherein the plurality of catalytic elements and the plurality of heat transfer elements are disposed within the reaction pathway in an alternating configuration defining a fluid flowpath from each element inlet side to each element outlet side.

In one illustrative embodiment, the interior wall, on a side opposite the reaction pathway, defines an interior plenum. To be more specific, the interior wall separates the reaction pathway from an interior plenum. In one illustrative embodiment, the interior plenum functions as a reactor inlet pathway. In another illustrative embodiment, the interior plenum functions as a reactor outlet pathway. In yet another illustrative embodiment, the interior wall is thermally conductive; and a supplementary heater, such as a conventional fossil fuel burner or a conventional reactor capable of sustaining any other exothermic reaction, is disposed within the interior plenum such that, functionally under operative conditions, heat generated by the supplementary heater is thermally conducted through the interior wall into the reaction pathway. The aforementioned embodiments will be explained in greater detail in the following description.

In another embodiment, this invention provides for a method of conducting an endothermic chemical reaction, comprising:

(a) providing a catalytic solar reactor comprising a reaction pathway having a reactor inlet and a reactor outlet, the pathway bounded by an exterior wall and an interior wall; wherein the exterior wall comprises a solar radiation receiver disposed in thermal communication with the reaction pathway; and further wherein the reaction pathway has disposed therein the following structures:

(a)(i) a plurality of catalytic elements, each catalytic element comprising a porous material having a catalyst supported thereon; the porous material comprising a mesh having an ultra-short-channel-length; each catalytic element further comprising a first flowpath from a first inlet side to a first outlet side;

(a)(ii) a plurality of heat transfer elements, each heat transfer element comprising a porous, thermally-conductive material substantially lacking catalytic activity; each heat transfer element further comprising a second flowpath from a second inlet side to a second outlet side; and (a)(iii) further wherein the plurality of catalytic elements and the plurality of heat transfer elements are disposed within the reaction pathway in an alternating configuration defining a reaction pathway from each element inlet side to each element outlet side;

(b) exposing the solar radiation receiver to solar radiation so as to transfer heat to the reaction pathway;

(c) feeding a reactant stream through the thusly-heated reaction pathway from each element inlet side to each element outlet side; and (d) contacting the reactant stream with the catalyst as the reactant stream passes through the reaction pathway, the contacting occurring under process conditions sufficient to produce a product stream.

Aspects of the invention are illustrated in the embodiments shown in FIGS. 1-7, as explained in detail hereinafter. With respect to FIG. 1, an embodiment 100 of the invention is depicted in a transverse cross-sectional view. In this embodiment, the reactor 100 has a modified triangular shape, in which exterior wall 1 is curved to form two sides 1a and 1b of a triangle, with apex 7 at the top of the curve. Exterior wall 1 is constructed from an essentially seamless solar radiation receiver. A third exterior wall 9 completes the triangle shape. Exterior wall 9 is attached at edges 3 and 5 to the exterior wall 1, respectively, to sides 1a and 1b. Interior wall 11 is disposed parallel to exterior wall 1; and consequently is also curved to form interior wall of sides 11a and 11b. The exterior wall 1 and the interior wall 11 define a reaction pathway 15. Interior wall 11, on a side opposite the reaction pathway 15, further defines an interior plenum 13. Reactor inlet 17 provides entry via a plurality of distribution inlets 19 into the reaction pathway 15; while interior plenum 13 and reactor outlet 21 provide an exhaust pathway from the reactor 100. The reaction pathway 15 has disposed therein, in alternating configuration, a plurality of catalytic elements 23, having a catalyst 25 supported thereon, and a plurality of heat transfer elements 27.

Figure 1:
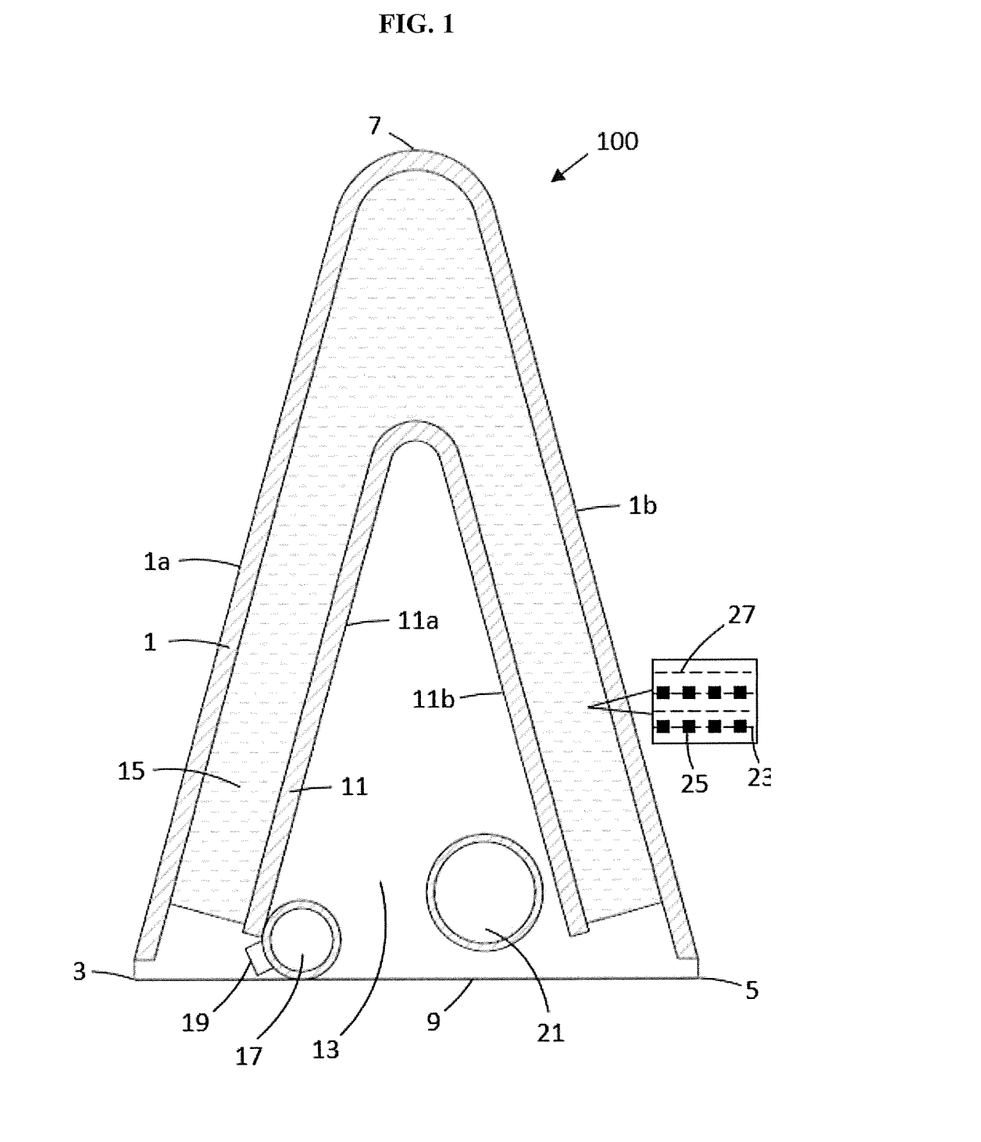
FIG. 1 illustrates a transverse cross-sectional view of an embodiment of the catalytic solar reactor of this invention.
Figure 2:
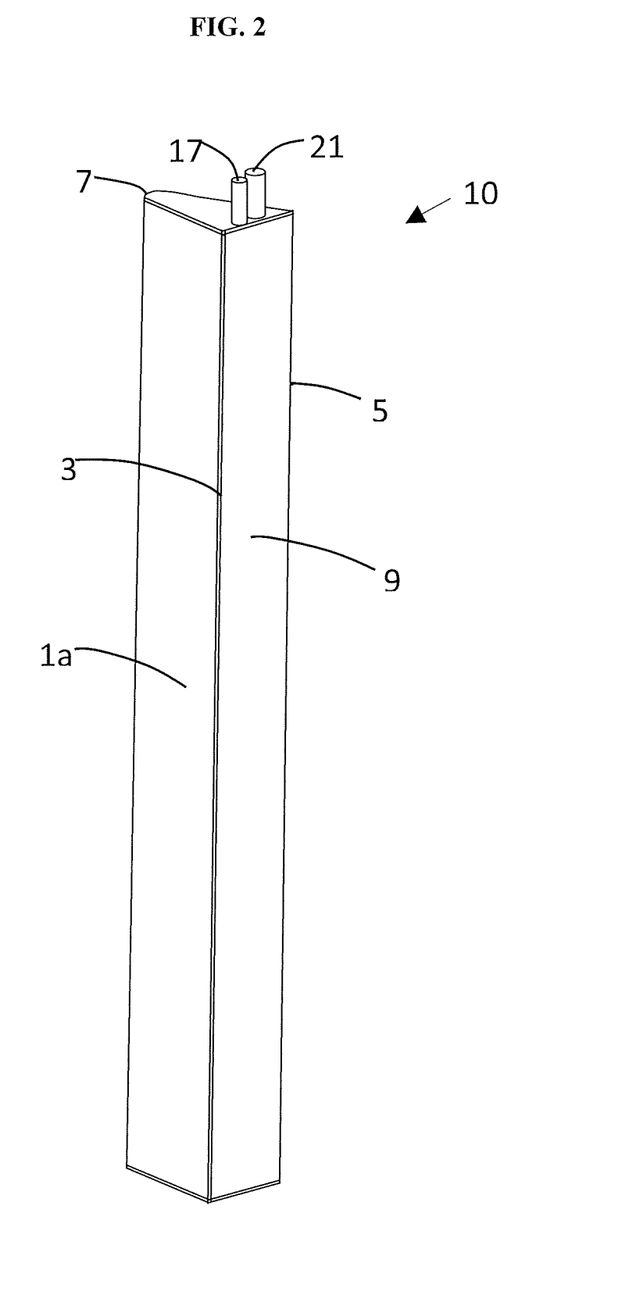
FIG. 2 illustrates an isometric external view of the embodiment of the catalytic solar reactor of this invention depicted in FIG. 1.

FIG. 2 illustrates the same embodiment 100 of the catalytic solar reactor of this invention from an exterior isometric view. The reactor extends longitudinally in the modified triangular shape with views of side 1a of exterior wall 1 and of third exterior wall 9, as well as curved apex 7. Again, exterior wall 1a comprises the solar radiation receiver, which is joined to exterior wall 9 along edge 3. Edge 5 seams the third exterior wall 9 to, in this view, the back wall 1b of the triangular-shaped reactor. The reactor includes the reactor inlet 17 for feeding a reactant flowstream into the interior reaction pathway and the outlet 21 for exhausting a reaction product stream from the interior reaction pathway, as seen as well in FIG. 1.

Figure 3:
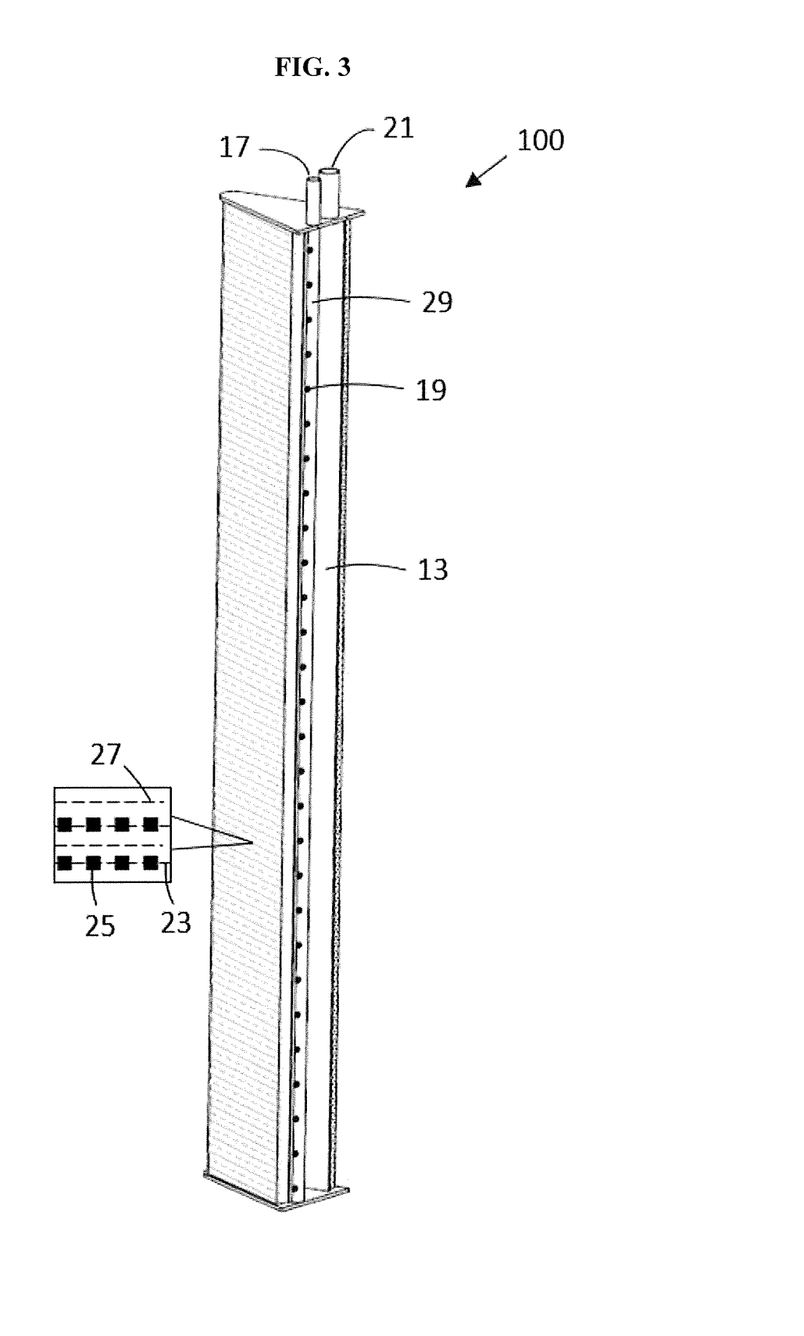
FIG. 3 illustrates an isometric view of the embodiment of the catalytic solar reactor depicted in FIG. 2 with its radiation receiver removed to expose internal components.

FIG. 3 illustrates the same embodiment 100 with its three exterior walls [FIG. 1 (1a/1b/9)] removed, so as to illustrate internal components. The reactor inlet 17 is seen to fluidly communicate with an interior inlet pathway 29 extending along the length of the reactor. The interior inlet pathway 29 comprises a plurality of distribution inlets 19, which fluidly connect the interior inlet pathway 29 with the reaction pathway containing the plurality of catalytic elements 23 having catalyst 25 supported thereon and the plurality of heat transfer elements 27, which features are disposed in thermal communication with the exterior solar radiation receiver (FIG. 1 (1)). The plurality of catalytic elements 23 and the plurality of heat transfer 27 elements are further disposed in fluid communication with the interior plenum 13 that itself fluidly communicates with the reactor outlet 21.

Functionally, the solar catalytic reactor 100 of FIGS. 1-3 converts sunlight into heat via the solar radiation receiver 1, which heat is transmitted via conduction and convection to the plurality of catalytic elements 23 and the plurality of heat transfer elements 27. A reaction fluid (reactant stream) is passed through the reactor inlet 17 into the interior inlet pathway 29, from thence through the distribution inlets 19, and then into the reaction pathway 15, where the reaction fluid contacts with the heated plurality of catalytic elements 23 supporting catalyst 25. There, the reaction fluid is converted into chemical products, which exit the reactor via the interior plenum 13 and reactor outlet 21. The heat transfer elements 27 aid in providing heat uniformly to the catalytic elements 23 along the entire reaction pathway 15. As well, the heat transfer elements 27 modulate and control the rate of chemical reaction occurring therein by providing a heat reserve to the catalytic elements 23 or by conducting heat away from the catalytic elements 23 depending upon the specific design.

Figure 4:
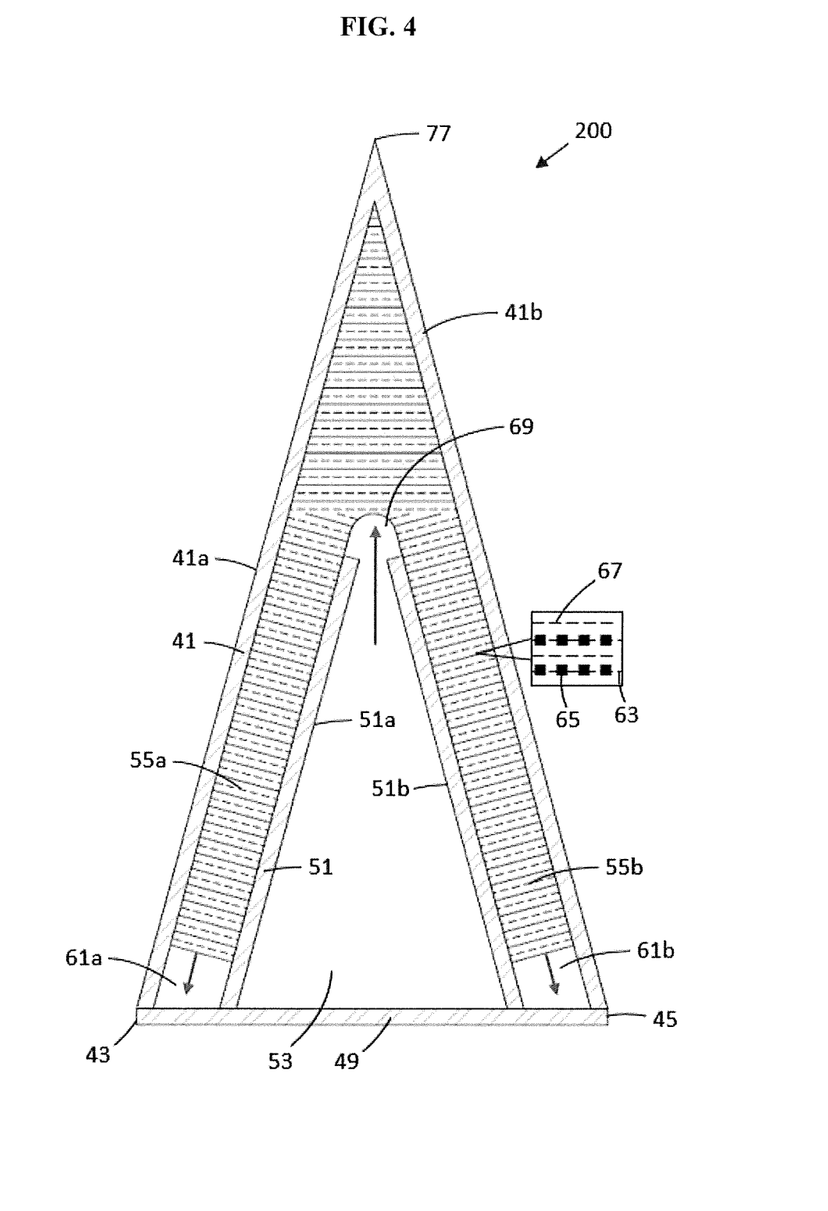
FIG. 4 illustrates a transverse cross-sectional view of another embodiment of the catalytic solar reactor of this invention.

FIG. 4 depicts a transverse cross-sectional view of another embodiment 200 of the catalytic solar reactor of this invention. Again, a triangular shape is visible; however, in this embodiment apex 77 of the triangle is a sharp point rather than a smooth arc. An exterior solar radiation receiver 41 is split into two sides 41a and 41b. A third wall 49 completes the exterior housing. Third wall 49 is seamed along edges 43 and 45 to the solar radiation receiver at sides 41a and 41b, respectively. Interior wall 51 is split into sides 51a and 51b, which are disposed in parallel configuration relative to the exterior walls 41a and 41b, respectively, thereby defining reaction pathways 55a and 55b. The interior walls 51a and 51b further define the interior plenum 53. The reaction pathways 55a and 55b have disposed therein, in alternating configuration, a plurality of catalytic elements 63 having a catalyst 65 supported thereon and a plurality of heat transfer elements 67. Radiation collected via the exterior solar radiation receiver 41 is converted into heat, which is transmitted conductively and convectively to the split reaction pathways 55a and 55b. It should be appreciated that the reaction pathway of FIG. 4 provides for a different flow architecture as compared with that of FIG. 1. Specifically in FIG. 4, interior plenum 53 receives the input of the reactant fluid stream, which is then provided to the reactor inlet situated at the interior inlet apex 69. At the inlet apex 69, the reaction flow stream splits along the two reaction pathways 55a and 55b, then exits at two reactor outlets 61a and 61b.

Figure 5:
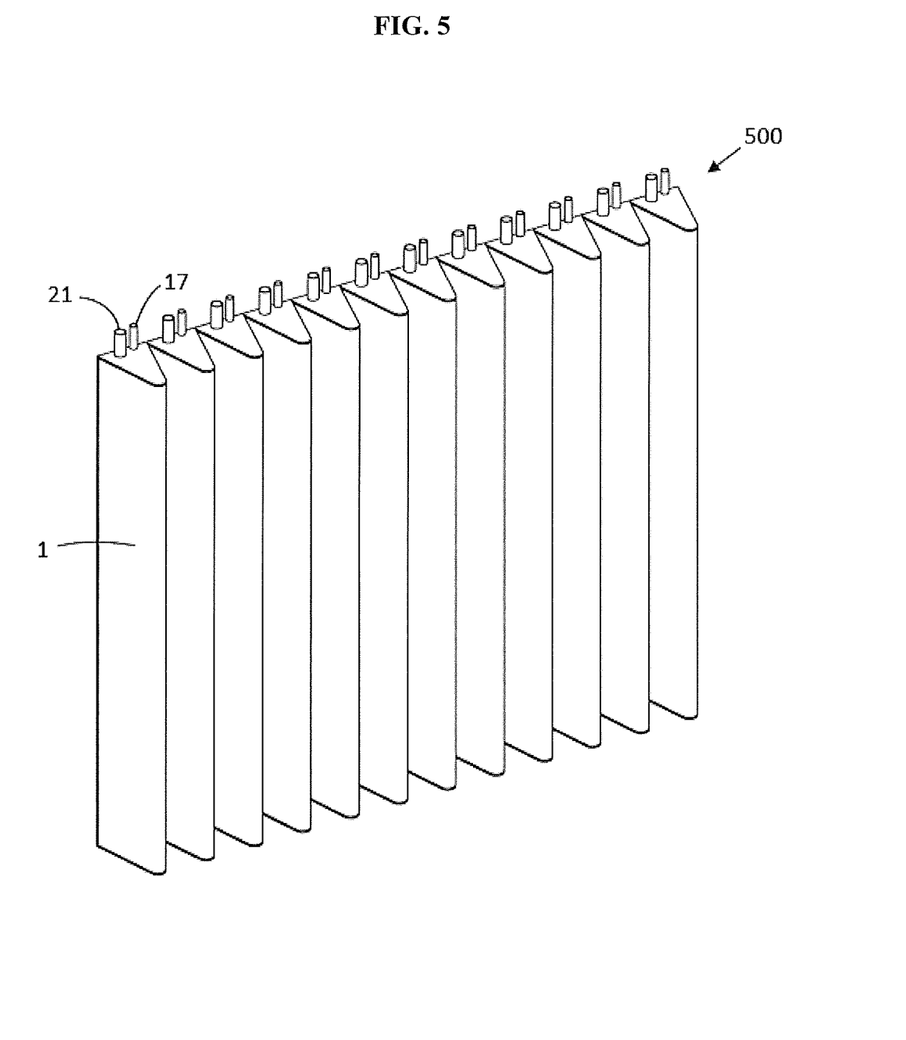
FIG. 5 illustrates an isometric view of a plurality of catalytic solar reactors of this invention assembled into a larger array for field purposes.

FIG. 5 illustrates another embodiment 500 of this invention in an isometric external view, in which a plurality of catalytic solar reactors of the embodiment type 100 depicted in FIG. 1, having a plurality of external solar radiation receivers 1, are disposed in a multi-reactor array. One skilled in the art will understand that a primary reactor feed line would be fluidly connected to each of the plurality of reactor inlets 17; and a primary product outlet line would be fluidly connected to each of the plurality of reactor outlets 21, so as to distribute, respectively, reaction fluid into the system array and reaction product fluid out of the system array.

The catalytic solar reactor of this invention comprises, as an integral component, a solar radiation receiver disposed as an exterior wall of the solar reactor. The art describes many different designs for solar radiation receivers, any of which is suitably employed in this invention. Generally, the solar radiation receiver comprises an absorber plate constructed of an acceptable thermally-conductive material, typically a metal, such as copper, aluminum, or any alloy capable of withstanding temperatures under operating conditions including, for example, Inconel 600, Haynes 230, and Haynes 214 alloys, and other nickel alloys. The absorber plate itself is painted or glazed with a dark-colored radiation-absorbing material, such as black paint. Typically, a transparent glaze covers the dark-colored absorber plate. Functionally, the solar radiation receiver collects and may also concentrate solar radiation, then further converts the radiation to heat, and then transmits the heat to the reaction pathway of the reactor where the chemical reaction occurs. Insulation is typically installed around non-collecting parts of the solar radiation receiver so as to minimize heat losses to the environment.

Solar radiation receivers are constructed in a variety of shapes, for example, as boxes and plates, as tubes, as parabolic surfaces, troughs, and various other forms with intentionally-designed angles and points for the purpose of maximizing solar radiation collection and minimizing radiation scattering and losses. In one embodiment, the solar radiation receiver comprises a non-concentrating solar collector, such that an area that intercepts the solar radiation is essentially equal to the area that absorbs the solar radiation. In another embodiment, a plurality of solar collectors intercept radiation over a large area, and then the intercepted radiation is concentrated and focused onto the solar radiation receiver. In this latter embodiment, the area intercepting and collecting the solar radiation is much larger than the absorption area of the solar radiation receiver. Non-limiting examples of suitable radiation receivers desirably employed in this invention include the solar receivers manufactured by Victory Energy (Collinsville, Okla.), Abengoa Solar (Spain), and Acciona Solar Power (Nevada).

Typically, the solar radiation receiver of the apparatus of this invention is constructed to receive from about 100 $kW/m^2$ to about 500 $kW/m^2$ solar irradiance, based on a planar receiver area normal to the direction of direct or reflected solar irradiance. In a preferred embodiment, the solar radiation receiver of the apparatus of this invention is designed and constructed so as to absorb from about 50 percent to about 100 percent of received irradiated energy, preferably, from about 70 percent to about 99 percent of the received irradiated energy. In another embodiment the solar radiation receiver is constructed with planar dimensions, normal to direct or reflected solar irradiance, of from 1 $m^2$ to 200 $m^2$, preferably, of from 20 $m^2$ to 50 $m^2$.

The reaction pathway is bounded on one side by the aforementioned thermally-conductive solar radiation receiver (exterior wall); while on the other side the reaction pathway is bounded by the interior wall disposed inside the reactor, the latter being unexposed and non-radiation collecting. The interior wall itself has a first side facing the reaction pathway and an opposite or second side facing and defining the reactor's interior plenum. As compared to the exterior wall, note that not all of the interior wall or walls need to be fixed, so as to allow for differential thermal expansion. The interior wall is constructed, in one embodiment, of a substantially non-thermally-conductive material, such as a ceramic, or a metal oxide, such as silica, alumina, titania, or zirconia; or alternatively, in another embodiment from a thermally conductive material, such as copper or aluminum, or any suitable alloy including Haynes 600, Haynes 230, Haynes 214 alloys and other nickel alloys. In the instance of a non-thermally conductive material, typically, the interior wall on its side facing the interior plenum is covered with an insulating material, such as fiberglass, to retard heat losses from the reaction pathway into the interior plenum within the reactor. In the instance wherein the interior wall is thermally-conductive, a supplementary heater, such as a conventional fossil fuel burner or, more generally, any apparatus for conducting an exothermic reaction, is typically disposed within the interior plenum. Under operating conditions, the supplementary heater is employed to provide heat, which is thermally conducted through the interior wall into the reaction pathway. This embodiment with the supplementary heater is particularly useful whenever the solar radiation receiver is turned down, for example, at night or in inclement weather or during maintenance. At such times, the supplementary heater provides heat to the reaction pathway so as to minimize downtime in operating the chemical reaction occurring therein.

Figure 6:
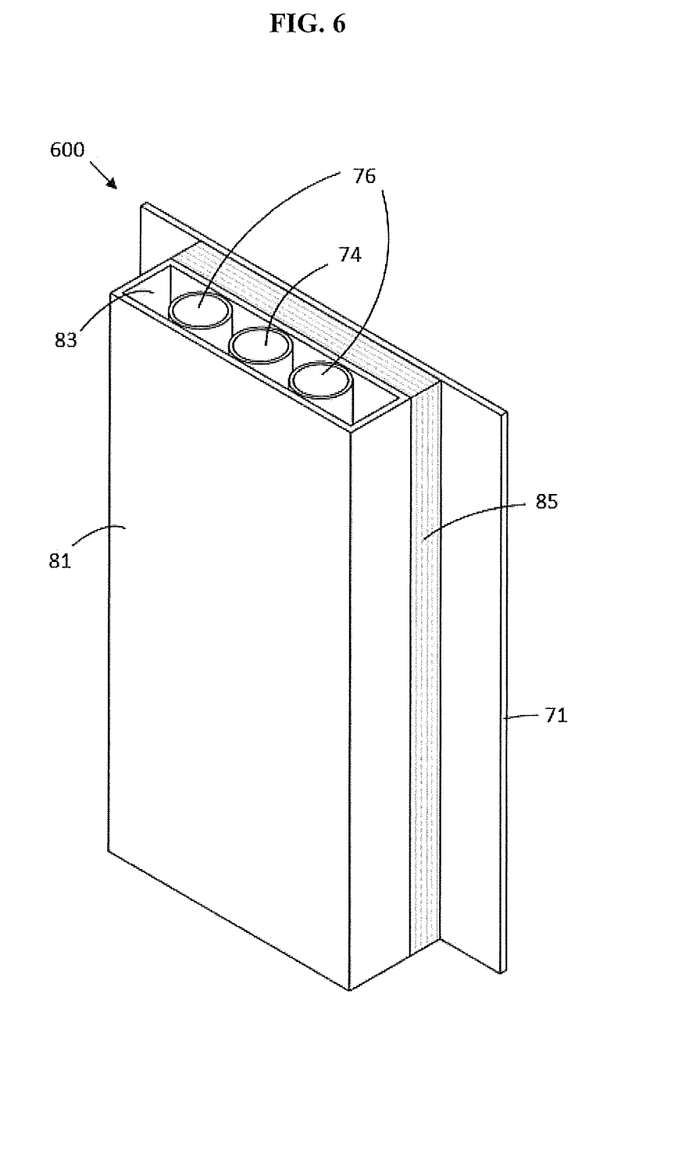
FIG. 6 illustrates an isometric view of an embodiment of the catalytic solar reactor of this invention having incorporated therein a plurality of fossil fuel burners.
Figure 7:
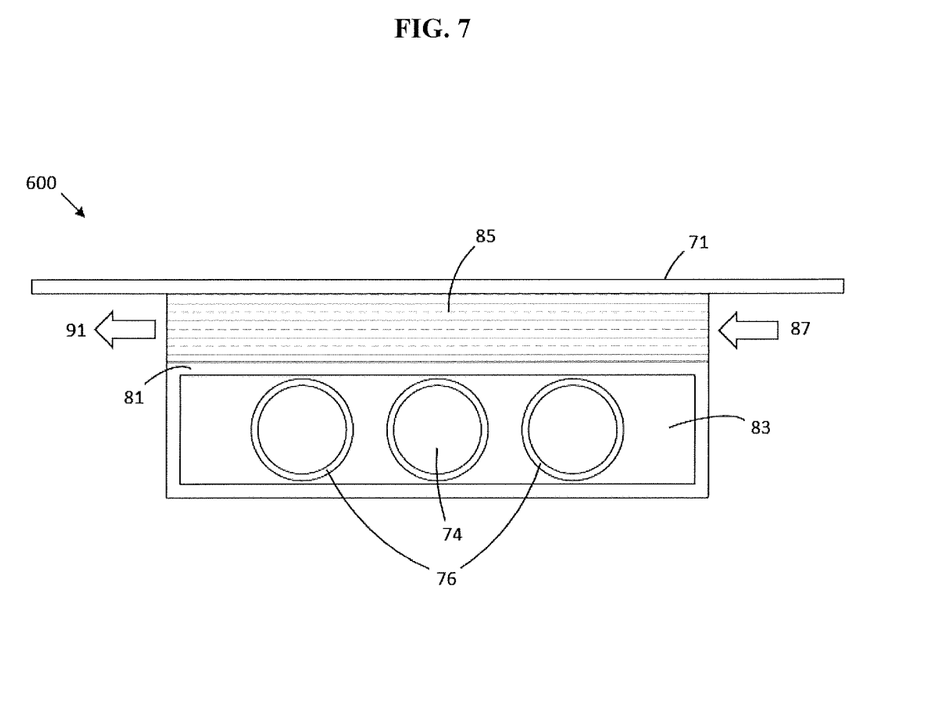
FIG. 7 illustrates a transverse view of the embodiment of the catalytic solar reactor depicted in FIG. 6.

FIG. 6 illustrates in isometric view an embodiment 600 of the catalytic solar reactor of this invention further incorporating a plurality of conventional fossil fuel burners. FIG. 7 illustrates this same embodiment 600 in a transverse view. A solar receiver 71 provides an exterior wall for collecting solar radiation and transferring heat collected therefrom into a reaction pathway 85. The reaction pathway 85 is occupied by a plurality of catalytic elements and a plurality of heat transfer elements as previously described, but not specifically called out in FIGS. 6 and 7. Reaction fluid enters the reaction pathway 85 via a reactor inlet 87; whereas product fluid exits the reaction pathway 85 via reactor outlet 91. An interior wall unit 81 functions in various capacities: (a) to define a back wall of the reaction pathway 85, (b) to define the interior plenum 83 that holds the fossil fuel burner(s) or combustor(s) 76, and (c) to provide an exhaust pathway exhausting fossil fuel combustion products. Further to FIGS. 6 and 7, a burner inlet 74 disposed in the interior plenum 83 functions as an inlet for a mixture of fossil fuel and air; while burners 76 function to combust the mixture to form combustion products with release of heat, which is conducted through the thermally-conductive wall 81 into the reaction pathway 85.

The reaction pathway defined by the exterior and interior walls of the solar reactor is configured in any shape providing for a fluid flowpath from the reactor inlet to the reactor outlet, as illustrated for example in any of FIGS. 1, 4, and 7. In one embodiment, the shape of the reaction pathway is a straight-through path, as seen for example in FIG. 7. In another embodiment, the shape of the reaction pathway is angled, curved or serpentine, as dictated by the design of the solar radiation receiver, and as seen for example in FIGS. 1 and 4. Solar radiation receivers often have sharp angles and turns to facilitate maximum capture of solar radiation while retarding radiation losses to the environment. As a consequence, the reaction pathway may also have corresponding angles, curves, or serpentine structure.

Each catalytic element housed within the reaction pathway comprises at least one porous material having a catalyst supported thereon. One side of the porous material is defined as an inlet (herein, the first inlet) for the purposes of fluid flow; whereas an opposite side of the porous material is defined as an outlet (herein, the first outlet) for the purposes of fluid flow. In one illustrative embodiment, the porous material comprises a mesh, that is, a reticulated net or screen constructed from a solid framework structure defining a plurality of pores, cells, or channels. In one illustrative embodiment, the mesh is characterized by an ultra-short-channel-length, defined as a length ranging from about 25 microns to about 500 microns from inlet to outlet. The porous material is typically constructed from any material capable of withstanding the intended operating temperatures, which generally range from about 150° C. to about 1,400° C. depending upon the chemical process under consideration. Such materials include metallic and ceramic materials of suitable temperature durability. Non-limiting examples of suitable metallic materials include those constructed from stainless steel, nickel-chromium-iron alloys, iron-chromium alloys, and iron-chromium-aluminum alloys. The term "ceramic" refers to inorganic non-metallic solid materials with prevalent covalent bonds, including but not limited to metallic oxides, such as oxides of aluminum, silicon, magnesium, zirconium, titanium, niobium, and chromium, as well as zeolites and titanates. Reference is made to U.S. Pat. Nos. 6,328,936 and 7,141,092, detailing layers of ultra-short-channel-length ceramic mesh comprising woven silica, both patents incorporated herein by reference.

In one exemplary embodiment, the mesh comprises a MICROLITH® brand ultra-short-channel-length mesh (Precision Combustion, Inc., North Haven, Conn., USA), a description of which is found, for example, in U.S. Pat. No. 5,051,241, incorporated herein by reference. Generally, the mesh comprises short channel length, low thermal mass monoliths, which contrast with prior art monoliths having longer channel lengths. For purposes of this invention, the term "ultra-short-channel-length" refers to a channel length in a range from about 25 microns ($\mu$m) (0.001 inch) to about 500 $\mu$m (0.02 inch). In contrast, the term "long channels" pertaining to prior art monoliths refers to channel lengths of greater than about 5 mm (0.20 inch) upwards of 127 mm (5 inches). In another embodiment, the channel length is no longer than the diameter of the elements from which the mesh is constructed; thus, the channel length may range from 25 $\mu$m (0.001 inch) up to about 100 $\mu$m (0.004 inch) and preferably not more than about 350 $\mu$m (0.014 inch). In view of this ultra-short channel length, the contact time of reactants with the mesh and catalyst supported thereon advantageously ranges from about 5 milliseconds (5 msec) to about 350 msec.

The porous material, preferably the MICROLITH brand ultra-short-channel-length mesh, typically comprises from about 100 to about 1,000 or more flow channels per square centimeter. More specifically, the porous material is configured with a plurality of channels or pores having a diameter ranging from about 0.25 millimeters (mm) to about 1.0 mm, with a void space greater than about 60 percent, preferably up to about 80 percent or more. A ratio of channel length to diameter is generally less than about 2:1, preferably less than about 1:1, and more preferably, less than about 0.5:1. MICROLITH brand meshes can be manufactured in the form of woven wire screens, woven ceramic fiber screens, pressed metal or ceramic screens; or they can be manufactured by perforation and expansion of a thin metal sheet as disclosed in U.S. Pat. No. 6,156,444, incorporated herein by reference; or alternatively manufactured by 3-D printing or by a lost polymer skeleton method.

In another exemplary embodiment, the porous material of the catalytic elements is constructed of an analogous porous structure of metal or ceramic comprising an interconnected network of solid struts defining a plurality of pores of an open-cell configuration. The pores can have any shape or diameter; but typically, a number of pores that subtend one inch designate a "pore size," which for most purposes ranges from about 5 to about 80 pores per inch. The relative density of such structures, taken as the density of the structure divided by the density of solid parent material of the struts, typically ranges from about 2 to about 15 percent. Structured porous materials are commercially available in a variety of compositions capable of withstanding the operating temperature of the reactor.

The catalytic elements support a catalyst capable of facilitating the chemical process intended to be operated within the catalytic solar reactor. One skilled in the art will know how to select a suitable catalyst, because the art is replete with description of specific catalysts useful for specific chemical processes. As an example, one finds in the art the following reference to Fischer-Tropsch catalysts: Nikolaos E. Tsakoumis, Magnus Rønning, Øyvind Borg, Erling Ryttera, Anders Holmen, "Deactivation of cobalt based Fischer-Tropsch catalysts: A Review," Catalysis Today 154 (2010) 162-182; as well as the following reference to catalysts for dry reforming carbon dioxide with hydrocarbons (e.g., methane) to produce syngas: John F. Múnera, Silvia Irusta, Laura M. Cornaglia, Eduardo A. Lombardo, Deborah Vargas Cesar, Martin Schmal, "Kinetics and reaction pathway of the $CO_2$ reforming of methane on Rh supported on lanthanum-based solid," Journal of Catalysis 245 (2007) 25-34. Likewise, the deposition of the catalytic metal(s) onto the catalytic elements is implemented by any method known in the art. Alternatively, finished catalysts comprising catalytic metal(s) supported on MICROLITH brand ultra-short-channel-length mesh may be obtained from Precision Combustion, Inc., North Haven, Conn.

The plurality of catalytic elements is distributed along the reaction pathway in a number of sets of such elements. The number of catalytic elements in any set varies as desired from set to set. In one illustrative embodiment, each set contains an identical number of catalytic elements, typically ranging from 1 to about 5 catalytic elements per set. In another embodiment, each set independently contains from 1 to about 5 catalytic elements.

Each heat transfer element comprises at least one porous, thermally-conductive material substantially lacking catalytic activity. Each heat transfer element further comprises an inlet (herein, the second inlet) and an outlet (herein, the second outlet) for the purposes of fluid flow. The term "porous" means that each heat transfer element comprises a plurality of pores or channels extending from the second inlet to the second outlet sufficient to provide through flow of reactant and product fluids. In one embodiment, the porous heat transfer element has an ultra-short-channel-length ranging from about 25 microns (25 µm) to about 500 microns 500 (µm) in length, with optionally, a pore density ranging from about 100 pores per square inch (100 ppi) to about 1,000 ppi. One such illustrative embodiment thereof is illustrated by the MICROLITH brand ultra-short-channel-length mesh described hereinabove (Precision Combustion, Inc.). In another illustrative embodiment, the porous material of the heat transfer element has a channel length ranging from about 50 microns (50 µm) up to about 25 millimeters (25 mm) in length. This latter embodiment is illustrated by a honeycomb monolith or a monolith structure with square, rectangular, hexagonal, circular or ellipsoidal passageways, or some combination thereof.

The term "thermally-conductive", as it pertains to the heat transfer elements, refers to any material of acceptable conductive solid-to-solid heat transfer. The skilled person will recognize that such thermally conductive materials include metallic elements; but ceramic materials may be suitably thermally conductive at temperatures above about 1,000° C. Non-limiting examples of suitable metallic materials include copper, aluminum, titanium, niobium, and standard and high temperature stainless steels, iron-chromium alloys, iron-chromium-aluminum alloys including FeCrAlY, and nickel-chromium-aluminum alloys including NiCrAlY. Non-limiting examples of suitable ceramic materials include alumina, silica, zirconia, titania, and mixtures thereof; as well as mullite, cordierite and other alumina-silica compositions with or without magnesia, and further optionally containing yttria and/or lanthana, as well as ceria-zirconia ceramics.

Referring to the heat transfer elements, the phrase "substantially lacking catalytic activity" means that the heat transfer elements, irrespective of whether or not they contain quantities of catalyst, do not exhibit sufficient catalytic activity in the subject chemical process so as to influence or render an effect upon conversion of reactants or selectivity to products. In one embodiment, essentially no catalyst is present on the heat transfer elements, and catalytic activity resulting from the heat transfer elements is non-detectable. In another embodiment, catalyst is present on the heat transfer elements but in a non-effective quantity, typically on the order of less than 0.5 percent by weight, and preferably, less than about 0.05 percent by weight, such that catalytic facilitation of conversion and yield is less than about 2 percent, preferably, less than about 1 percent.

Each of the plurality of heat transfer elements may actually comprise a set of such elements. The number in each set varies depending upon the quantity of heat needed to be input to the reaction pathway. In one illustrative embodiment, each set of heat transfer elements comprises one monolithic structure (e.g., honeycomb). In another illustrative embodiment, each set of heat transfer elements comprises more than one monolithic structure, typically from 1 to 3. In another illustrative embodiment, each set of heat transfer elements is comprised of a selected number of layers of mesh ranging from 1 to about 5. The thickness of the monolithic structure or the number of layers can be identical or variable from set to set, as desired.

Referring to FIG. 1 herein, the skilled person will appreciate that the thickness of each set of catalytic elements relative to the thickness of each set of heat transfer elements depends upon the quantity of heat needed to be transmitted into or out of the reaction pathway to maintain an essentially isothermal temperature along the reaction pathway or, alternatively, a desired temperature profile along the reaction pathway. For operability and as general guidance, we have found that the thickness of each catalytic element typically ranges from about 1.0 percent to about 100 percent of the thickness of each heat transfer element. Or, the total length occupied by the catalytic elements in a series of catalytic and heat transfer elements is from about 1.0 percent to about 50 percent. The thickness of the catalytic elements ranges from about 0.003 inch (75 microns, µm) to 0.25 inch (6.3 mm), preferably from 0.004 inch (100 µm) to 0.020 inch (500 µm), and more preferably from 0.006 inch (150 µm) to 0.014 inch (350 µm). The thickness of the heat transfer elements ranges from about 0.003 inch (75 µm) to 1.0 inch (25 mm), preferably from 0.06 inch (1.5 mm) to 0.50 inch (12.5 mm), and more preferably from 0.10 inch (2.5 mm) to 0.25 inch (6.3 mm). A repeating group of catalytic and heat transfer elements can be considered to be one or more catalyst elements adjacent to one or more heat transfer elements. For example, a 0.007 inch (175 µm) thick catalytic element adjacent to two 0.125 inch (3.1 mm) heat transfer elements can be considered one repeat unit, in which case the catalytic elements occupy 2.72 percent of the total length of the repeat unit. Adjacent repeat units, in either the upstream or downstream locations, can be the same repeat unit or consist of a different combination of catalyst and heat transfer elements.

The plurality of catalytic elements and plurality of heat transfer elements are disposed within the reaction pathway in alternating configuration. One embodiment comprises a stack of alternating catalytic and heat transfer elements disposed longitudinally along the length of the reactor. In this embodiment, at least one edge of each element contacts the solar radiation receiver facilitating heat transfer directly from the radiation receiver to each element and the reaction pathway. In this embodiment, fluids typically flow in a direction perpendicular to the transverse face of the element, that is, in parallel with the direction of minimum dimension. Another embodiment comprises a nest of alternating catalytic and heat transfer elements starting with a face of the initial element directly contacting the radiation receiver along its entire longitudinal length; and then nesting alternating elements inwardly towards the interior wall. In this second embodiment, only the initial element directly contacts the radiation receiver; and heat is transferred in an inward direction from the initial element to each sequentially nested element. Moreover, fluids typically flow in a transverse direction in this embodiment. As well, other embodiments are permissible wherein the fluid flow and the catalytic and heat transfer elements are oriented in other directions with respect to the radiation receiver.

It should be further appreciated that the catalytic solar reactor of this invention does not comprise an electrical circuit that functionally feeds electricity into the catalytic elements or heat transfer elements. Accordingly, no electrical resistive heating is provided to the reaction pathway of this reactor and its associated catalytic and heat transfer elements. Rather, the solar reactor of this invention is heated passively through conduction of heat obtained primarily from solar radiation into the catalytic and heat transfer elements intercalated along the reaction pathway. In one embodiment, heat is also obtained from a supplemental heater, such as a conventional burner, as detailed hereinbefore. The catalytic solar reactor is particularly suitable for use in endothermic chemical processes that primarily obtain their required heat from the solar radiation receiver and secondarily from a supplemental heater.

While not bound to any theory or mechanism, the catalytic solar reactor of this invention is designed to enable isothermal or close-to-isothermal conditions within the catalytic elements by providing sufficient thermal energy, via conduction through the heat transfer elements, to balance the rate of heat removal due to an endothermic chemical process occurring in the volume occupied by the catalytic elements. Enabling isothermal operation avoids operating the catalyst elements at unacceptably low temperatures that would otherwise reduce volumetric reaction rates, even beyond what would occur if all of the heat transfer elements were replaced by catalytic elements. In other words, optimally, the catalytic solar reactor of this invention, with alternating catalytic and heat transfer elements, results in higher volumetric productivity, as compared to an identically-sized reactor without heat transfer elements, and also results in a significant reduction and cost savings due to reduced catalyst use.

One skilled in the art will appreciate that one goal of the present invention is balancing the location and volume occupancy of the heat transfer elements to account for required heat transfer in order to maintain essentially all catalytic elements at nearly the same temperature regardless of location within the reactor. In one embodiment the arrangement of catalytic to heat transfer elements is regular and periodic; in another embodiment gradients in volume occupancy occur from one end to the other within the reactor, for example, increase and then decrease, or decrease then increase, or occur in non-regular fashion. In yet another embodiment, variations occur from reactor to reactor in a multi-reactor array of catalytic solar reactors of this invention. The aforementioned embodiments and variations depend on the extent of energy needed to be input or removed from the catalytic elements, and on the rates of conductive heat transfer from external to the solar radiation receiver, and thence to or from the heat transfer elements; as well as depending upon the rate of convective heat transfer to or from the heat transfer elements by the reactant, diluent and product fluids flowing through the reactor to the catalytic elements. These embodiments and arrangement variations are suitable for reactors with triangular, circular, ellipsoidal, square, rectangular, hexagonal, and other shapes in cross section perpendicular to the primary fluid flow direction. In one illustrative embodiment, any number of reactors, for example, from two to 50, can be assembled into a multi-reactor array as illustrated, for example, in FIG. 5. The reactors can be externally or internally heated or cooled by heat transfer fluids, by air, or other fluid flow via forced or natural convection, by steam generation or condensation, by external or internal exothermic or endothermic reactions, by radiation either photonic or radioactive, or by other means of heating or cooling of objects as practiced in industrial processes.

Under operating conditions, the catalytic solar reactor of this invention functions substantially isothermally. This means that the rate of heat consumption or generation by essentially all catalytic elements contained in the reactor for either endothermic or exothermic reactions is balanced by conduction, either into or out of, respectively, the reactor by the heat transfer elements, so as to maintain essentially all catalytic elements at substantially the same operating temperature. Specifically, a maximum variation between catalyst elements is typically no more than about 10 percent, as measured in absolute temperature terms (i.e. Kelvin or Rankine), with a variation of less than 5 percent preferred.

EXAMPLE

An array of catalytic solar reactors is constructed with an external array of solar radiation receivers as illustrated in FIG. 5. The interior of each solar catalytic reactor in the array is constructed as illustrated in FIG. 1. The array is positioned at the focal area of a heliostat field. (A heliostat is a device that includes a mirror that turns, so as to keep reflecting sunlight towards a predetermined target.) The array occupies a projected planar area of 25 m$^2$ normal to the direction of irradiance and receives a daily maximum power of 8.91 MW, assuming that the heliostat field and the solar receivers together have an overall efficiency of approximately 72 percent (72%), a daily maximum irradiance of 900 W/m$^2$ and 13,750 m$^2$ of heliostats. The array of reactors is supplied with feed streams consisting of carbon dioxide, natural gas, and process recycle. Calculated product compositions are determined based on reactor feeds, including typical natural gas and carbon dioxide feed compositions and recycle streams derived from downstream processes. Specifically, natural gas consisting of 95.6 percent methane (95.6% $CH_4$), 1.99 percent ethane (1.99% $C_2H_6$), 1.38 percent carbon dioxide (1.38% $CO_2$), 0.75 percent nitrogen (0.75% $N_2$), and 0.28 percent propane (0.28% $C_3H_8$) is fed at a flow rate of 0.117 mol/hr and is combined with carbon dioxide (100% $CO_2$) fed at a flow rate of 0.04 mol/hr, and with downstream recycle streams consisting of water (100 percent) fed at 0.08 mol/hr and a recycle feed consisting of 56.5 percent hydrogen (56.5% $H_2$), 1.17 percent methane (1.17% $CH_4$), 40.6 percent carbon monoxide (40.6% CO), 0.84 percent carbon dioxide (0.84% $CO_2$), and 0.92 percent nitrogen (0.92% $N_2$) fed at 0.029 mol/hr. The reactants are contacted in the catalytic solar reactor according to the combined endothermic reactions of Equations 1-5 hereinabove, at an inlet temperature of 615° C. A product gas is formed consisting of 64.7 percent hydrogen (64.7% $H_2$), 0.3 percent methane (0.3% $CH_4$), 0.8 percent water (0.8% $H_2O$), 33.6 percent carbon monoxide (33.6% CO), 0.4 percent carbon dioxide (0.4% $CO_2$), and 0.2 percent nitrogen (0.2% $N_2$), all exiting at a flow rate of 0.498 mol/hr, calculated at thermodynamic equilibrium at a reactor exit temperature of 925° C. Thus the 8.91 MW of power received by the reactor is used for both sensible heating of the reactants and for the chemical energy required to convert the reactants to products. In this example the solar radiation receivers of the total array, on a planar basis, receives 356.4 kW/m$^2$, which represents a concentration of approximately 397 suns.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A catalytic solar reactor comprising a reaction pathway having a reactor inlet and a reactor outlet, the reaction pathway defined by an exterior wall and an interior wall; wherein the exterior wall comprises a solar radiation receiver disposed in thermal communication with the reaction pathway; and further wherein the reaction pathway has disposed therein the following structures:
   (a) a plurality of catalytic elements, each catalytic element comprising a porous material having a catalyst supported thereon, each catalytic element further comprising a first flowpath from a first inlet side to a first outlet side;
   (b) a plurality of heat transfer elements directly attached to said exterior wall, each heat transfer element comprising at least one porous, thermally-conductive material substantially lacking catalytic activity; each heat transfer element further comprising a second flowpath from a second inlet side to a second outlet side; and
   (c) further such that the plurality of catalytic elements and the plurality of heat transfer elements are disposed within the reaction pathway in an alternating configuration defining a fluid flowpath from each element inlet side to each element outlet side.

2. The catalytic solar reactor of claim 1 wherein under operating conditions, the reactor functions via passive thermal conduction from the solar radiation receiver to the reaction pathway.

3. The catalytic solar reactor of claim 1 wherein under operating conditions, the reactor operates essentially isothermally within the plurality of catalytic elements.

4. The catalytic solar reactor of claim 1 wherein each of the plurality of catalytic elements is independently selected from metallic and ceramic materials.

5. The catalytic solar reactor of claim 4 wherein each of the plurality of catalytic elements is provided in the form of a mesh.

6. The catalytic solar reactor of claim 5 wherein the mesh has an ultra-short-channel-length ranging from 25 microns to 500 microns.

7. The catalytic solar reactor of claim 5 wherein the mesh comprises from 100 to 1,000 flow channels per square centimeter.

8. The catalytic solar reactor of claim 4 wherein each of the plurality of catalytic elements comprises a structured material having from 5 to 80 pores per inch.

9. The catalytic solar reactor of claim 1 wherein each of the plurality of catalytic elements independently comprises a set of from 1 to 5 catalytic elements.

10. The catalytic solar reactor of claim 1 wherein the catalyst is selected from a dry reforming catalyst or a Fisher-Tropsch catalyst.

11. The catalytic solar reactor of claim 1 wherein each of the plurality of heat transfer elements is independently selected from monolithic honeycombs and ultra-short-channel-length meshes.

12. The catalytic solar reactor of claim 11 wherein the monolithic honeycomb has a channel length ranging from 50 microns to 25 millimeters; or alternatively, the ultra-short-channel-length mesh has a channel length ranging from 25 microns to 500 microns.

13. The catalytic solar reactor of claim 1 wherein each of the plurality of heat transfer elements is constructed from a metallic composition.

14. The catalytic solar reactor of claim 1 wherein each of the plurality of heat transfer elements independently comprises a set of from 1 to 5 heat transfer elements.

15. The catalytic solar reactor of claim 1 wherein each of the plurality of heat transfer elements comprises no catalyst; or alternatively, comprises a catalyst in an amount less than 0.5 percent, based on total weight of the heat transfer element plus catalyst, so as to facilitate less than 1 percent additional conversion or yield under operating conditions.

16. The catalytic solar reactor of claim 1 wherein a thickness of each catalytic element ranges from 1 percent to 100 percent of a thickness of each heat transfer element.

17. The catalytic solar reactor of claim 1 wherein a total length occupied by the plurality of catalytic elements ranges from 1 percent to 50 percent of a total length of the sum of the catalytic elements plus the heat transfer elements.

18. The catalytic solar reactor of claim 1 wherein a thickness of a set of catalytic elements ranges from 75 microns to 6.3 millimeters, and a thickness of a set of heat transfer elements ranges from 75 microns to 25 millimeters.

19. The catalytic solar reactor of claim 1 wherein the solar radiation receiver is capable of receiving from 100 to 500 $kW/m^2$ solar irradiance, based on a planar receiver area normal to the direction of direct or reflected solar irradiance.

20. The catalytic solar reactor of claim 1 wherein the solar radiation receiver is capable of adsorbing from 50 percent to 100 percent of irradiated energy.

21. The catalytic solar reactor of claim 1 wherein the solar radiation receiver is constructed with planar dimensions, normal to direct or reflected solar irradiance, of from 1 $m^2$ to 200 $m^2$.

22. The catalytic solar reactor of claim 1 wherein a supplemental heater is disposed within an interior plenum of the catalytic solar reactor.

23. The catalytic solar reactor of claim 22 wherein the supplemental heater is a fossil fuel burner.

* * * * *